(12) United States Patent
Ramanathan et al.

(10) Patent No.: US 9,186,515 B2
(45) Date of Patent: Nov. 17, 2015

(54) SYSTEM AND METHODS TO FACILITATE PROVIDING THERAPY TO A PATIENT

(75) Inventors: Charulatha Ramanathan, Solon, OH (US); Harold Wodlinger, Thornhill (CA); Ping Jia, Solon, OH (US); Maria Strom, Mayfield Heights, OH (US)

(73) Assignee: Cardioinsight Technologies, Inc., Cleveland, OH (US)

( * ) Notice: Subject to any disclaimer, the term of this patent is extended or adjusted under 35 U.S.C. 154(b) by 0 days.

(21) Appl. No.: 14/127,130

(22) PCT Filed: Jul. 5, 2012

(86) PCT No.: PCT/US2012/045597
§ 371 (c)(1),
(2), (4) Date: Dec. 17, 2013

(87) PCT Pub. No.: WO2013/006724
PCT Pub. Date: Jan. 10, 2013

(65) Prior Publication Data
US 2014/0135866 A1 May 15, 2014

Related U.S. Application Data

(60) Provisional application No. 61/504,536, filed on Jul. 5, 2011, provisional application No. 61/546,083, filed on Oct. 12, 2011.

(51) Int. Cl.
*A61N 1/368* (2006.01)
*A61N 1/365* (2006.01)
*A61B 5/04* (2006.01)
(Continued)

(52) U.S. Cl.
CPC ............. *A61N 1/368* (2013.01); *A61B 5/0402* (2013.01); *A61B 5/04012* (2013.01); *A61B 5/4836* (2013.01); *A61N 1/36514* (2013.01); *A61N 1/36528* (2013.01); *G06F 19/3406* (2013.01); *G06F 19/3437* (2013.01); *G06F 19/3481* (2013.01); *A61B 5/04085* (2013.01); *A61B 5/7425* (2013.01); *A61B 2576/023* (2013.01); *A61N 1/3627* (2013.01); *A61N 1/3684* (2013.01)

(58) Field of Classification Search
None
See application file for complete search history.

(56) References Cited

U.S. PATENT DOCUMENTS

| 6,728,562 | B1 | 4/2004 | Budd et al. | |
|---|---|---|---|---|
| 7,933,649 | B1 * | 4/2011 | Atherton et al. | 607/9 |
| 2005/0090870 | A1 | 4/2005 | Hine et al. | |
| 2006/0253162 | A1 | 11/2006 | Zhang et al. | |

(Continued)

FOREIGN PATENT DOCUMENTS

| WO | WO 2005/046480 A1 | 5/2005 |
|---|---|---|
| WO | WO 2010/054320 A1 | 5/2010 |

*Primary Examiner* — Brian T Gedeon
(74) *Attorney, Agent, or Firm* — Tarolli, Sundheim, Covell & Tummino LLP

(57) ABSTRACT

A method can include providing (302) at least one parameter to control a therapy that is applied to at least one internal anatomical structure of a patient. Electrical data can be obtained from the patient (304), including electrical data acquired via a plurality of sensors during each of a plurality of iterations of the therapy. The electrical data can be analyzed (306) for a respective value of the at least one parameter of the therapy at each of the plurality of iterations of the applied therapy to compute an indication of at least one function of the at least one internal anatomical structure of the patient at each respective iteration of the applied therapy. The computed indication can be stored in memory (308). At least one parameter of the therapy can be adjusted (310) for delivery in a subsequent one of the plurality of iterations based on the indication of the at least one function.

32 Claims, 9 Drawing Sheets

(51) Int. Cl.
*A61B 5/0402* (2006.01)
*G06F 19/00* (2011.01)
*A61B 5/00* (2006.01)
*A61B 5/0408* (2006.01)
*A61N 1/362* (2006.01)

(56) References Cited

U.S. PATENT DOCUMENTS

2009/0053102 A2 2/2009 Rudy et al.
2009/0254140 A1 10/2009 Rosenberg et al.

* cited by examiner

SYSTEM AND METHODS TO FACILITATE PROVIDING THERAPY TO A PATIENT

CROSS-REFERENCE TO RELATED APPLICATIONS

This application is a National Stage Application filed under 35 U.S.C. §371 of PCT/US2012/045597, having a filing date of Jul. 5, 2012, which claims the benefit of U.S. Provisional Patent Application No. 61/504,536, filed Jul. 5, 2011, and entitled METHODS AND DEVICES FOR MEASURING AND OPTIMIZING VENTRICULAR SYNCHRONY IN CRT, and U.S. provisional patent application no. 61/546,083 filed Oct. 12, 2011, and entitled METHOD AND SYSTEM TO DETERMINE A SENSING ZONE TO FACILITATE ELECTROCARDIOGRAPHIC MAPPING AND ELECTRODE ARRANGEMENT FOR ECM. The entire contents of each of the above-identified patent applications are incorporated herein by reference.

TECHNICAL FIELD

This disclosure relates to systems and methods for providing therapy to a patient.

BACKGROUND

A variety of therapies can be provided to patients to treat a variety of medical conditions associated with internal anatomical structures. Such therapies can include applying a variety of external stimuli to the internal anatomical structure. As one example, cardiac resynchronization therapy (CRT) is a method of improving the mechanical function of the heart using electrical therapy (e.g., pacing both the right and left ventricles). Various techniques are utilized to determine a pacing site as well as to determine pacing parameters. Current mechanical and electrical measures tend to be qualitative and are highly operator dependent due to the complex nature of ventricular activation and the lack of quantitative comparisons between electrical activation and mechanical function.

SUMMARY

This disclosure relates to systems and methods to facilitate providing therapy to a patient, such as based on sensed electrical data.

As an example, a method can include providing at least one parameter to control a therapy that is applied to at least one internal anatomical structure of a patient. Electrical data can be obtained from the patient, including electrical data acquired via a plurality of sensors during each of a plurality of iterations of the therapy. The electrical data can be analyzed for a respective value of the at least one parameter of the therapy at each of the plurality of iterations of the applied therapy to compute an indication of at least one function of the at least one internal anatomical structure of the patient at each respective iteration of the applied therapy. The computed indication can be stored in memory. At least one parameter of the therapy can be adjusted for delivery in a subsequent one of the plurality of iterations based on the indication of the at least one function.

As another example, a method can include obtaining electrical data for a predetermined zone of a body surface of a patient, the electrical data obtained for the predetermined zone deterministically mapping to a predetermined region of interest of an organ of the patient. The method can also include analyzing the electrical data to compute an indication of at least one function of the predetermined region of interest of the organ of the patient. The indication of the at least one function of the predetermined region of interest of organ of the patient can be stored in memory and a corresponding output can be generated.

As another example, a method can include obtaining image data that includes at least one internal anatomical structure of the patient. The method can also include calculating dimensions associated with an organ of the patient based on the image data. The method can also include modifying dimensions of a generic model one of the organ to provide a modified model based on the calculated dimensions. The method can also include delivering a therapy having at least one parameter to treat the organ of the patient, the at least one parameter being variable during each of a plurality of iterations of the therapy. The method can also include obtaining electrical data from the patient based on electrical activity detected via a plurality of sensors, the electrical data including electrical activity detected in response to the therapy delivered at each of the plurality of iterations of the therapy. The method can also include correlating the electrical data to a corresponding region of interest of the modified model. The method can also include analyzing the correlated electrical data obtained for a respective value of the at least one parameter of the therapy at each of the plurality of iterations of the therapy to compute an indication of at least one function of the organ of the patient at each of the plurality of iterations of the therapy. The method can also include storing the indication of the at least one function of the organ of the patient in memory. The method can also include adjusting the at least one parameter of the therapy being delivered to the patient for a given one of the plurality of iterations in response to the computed indication of at least one function from another one of the plurality of iterations.

Each of such method, for example, can be implemented as a computer-implemented method or it can be implemented as instructions executable stored in a readable medium, such as may be executed by a processor.

DETAILED DESCRIPTION

Figure 1:
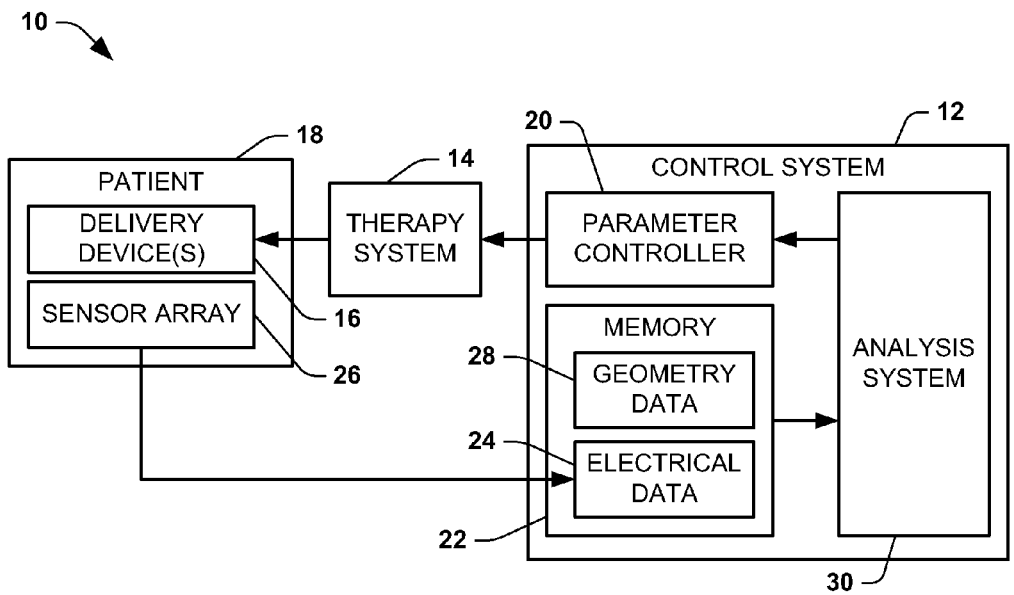
FIG. 1 depicts an example of a system that can be implemented to provide therapy for a patient.

This disclosure relates to systems and methods that can be utilized to facilitate providing therapy to a patient. As an example, the systems and methods can be employed to provide a quantitative assessment of heart function (e.g., synchrony) that is computed based on electrical information for one or more regions of the heart.

As another example, the systems and methods can be utilized to evaluate a function of an organ based on electrical activity distributed across one or more spatial regions of the organ. In the example, where the organ is the heart, the regions can include segmented regions (also referred to herein as segments) within one or more chambers of the heart. The evaluation further can include comparative or correlative statistics for the electrical activity among multiple heart chambers, such as may include the left and right chambers (e.g., ventricles) of the heart.

A therapy can be applied to a patient, such as cardiac resynchronization therapy (CRT), in which electrical stimulation can be applied to specific regions of the heart. Electrical data can be obtained in response to the application of the therapy, such as based on a plurality of electrodes. For example, the plurality of electrodes can be placed on a body surface of the patient. The electrodes can correspond to a predetermined zone of the body surface, which zone has been determined to map deterministically to a specific region of interest of the heart or other organ. The electrical data can be obtained at each of a plurality of iterations of an applied therapy. At each iteration, different therapy parameters can be used and the electrical data can be analyzed, such as based on a computational analysis. The analysis of the electrical data can be based on an application of the electrical data to one or more regions of the respective internal anatomical structure (e.g., heart) of the patient. As disclosed herein, the analysis and computations can be performed relative to generic anatomy, based on one or more simple images to a generic model as well as based on more sophisticated imaging modalities. In some examples, simple image data for a given patient can be utilized to adjust a generic model of an organ to accommodate some aspects of patient geometry (e.g., general organ dimensions). This approach employing simplified imaging can be contrasted with other mapping techniques where electrical data is mapped to a patient's own geometry according to more sophisticated (and expensive) imaging techniques, such as computed tomography or magnetic resonance imaging.

As used herein, the terms "internal anatomical structure" and "organ" are used interchangeably.

At least one value associated with the one or more parameters of the therapy can then be adjusted based on the analyzed electrical data at each iteration, such that the therapy can be applied based on the adjusted value(s) of the one or more parameters at a next iteration. Accordingly, the therapy, such as CRT, can be applied to the patient in a feedback manner.

As another example, the quantitative analysis can be computed to output one or more indices that quantify activation time heterogeneity and/or repolarization time heterogeneity. For instance, one or more indices can be computed to include one or more of a Global Interventricular Synchrony (GIS) Index, a Segmental Synchrony Index (SIS), an Intraventricular Conduction Index (ICI), or a late activation (LAI) index. Each index can be calculated based solely on measured electrical activity (e.g., without the need for mechanical data for the heart). For instance, the electrical activity can be measured via non-invasive methods. Systems and methods can generate graphical outputs based on these or other indications of synchrony to facilitate the assessment of cardiac function. As used herein, synchrony is intended to indicate a measure of synchrony between regions of the heart, which may be demonstrated in terms of synchrony and/or dyssynchrony.

In some examples, a quantitative assessment of synchrony can also be utilized to facilitate delivery of a therapy. For example, an indication of cardiac synchrony can be computed intraoperatively and used to guide administration of therapy to the patient (e.g., providing closed loop feedback during delivery of therapy). The guidance can include spatial guidance to locate one or more sites to which the therapy may be applied. Additionally or alternatively, the guidance can provide information to set and/or provide automated control for therapy parameters (e.g., a quantity and duration of a given therapy as well as a delay time between delivery of consecutive therapies). As used herein, the term "therapy parameters" thus is intended to encompass both the spatial guidance and control of electrical therapy parameters.

As a further example, the computed index can be computed and used as closed loop control to guide CRT therapy, such as taking into account both the delivery method (the accessible locations where a pacing lead can be anchored) and providing information about the health of the substrate. For determining the treatment parameters (e.g., location as well as stimulation parameters), each treatment parameter can be varied for a given patient and the index computed for a plurality of different treatment parameters. This process can be repeated and the results evaluated to ascertain treatment parameters to achieve desired therapeutic effect.

FIG. 1 depicts an example of a system 10 for providing therapy to a patient. The system 10 can be implemented in a standalone computer, a workstation, an application specific machine, or in a network environment in which one or more of the modules or data can reside locally or remotely relative to where a user interacts with the system 10.

The system 10 includes a control system 12 for controlling the application of the therapy in a closed-loop feedback manner. The control system 12 can be configured to provide control signals and/or control commands to a therapy system 14 that is coupled to one or more therapy delivery devices 16 that are coupled to a patient 18. As an example, the therapy delivery device(s) 16 can be configured as including one or more electrodes that can engage the internal anatomical structure of the patient 18. For instance, the therapy delivery devices 16 can be implemented as a catheter or pacing leads.

In the example of FIG. 1, the control system 12 includes a parameter controller 20 that is configured to set at least one value of one or more parameters of the therapy system 14, such as to control the signals and/or commands that are provided to the therapy delivery device(s) 16. As an example, the therapy delivery device(s) 16 can each provide an electrical stimulus to a selected portion of the anatomy of the patient 18 in an invasive or non-invasive manner based on the command signals and/or commands. In some examples, the therapy delivery device(s) 16 can be configured to provide electrical signals to stimulate regions of the heart of the patient 18 for cardiac resynchronization therapy (CRT), regions of the brain of the patient 18 for deep brain stimulation (DBS) therapy, or a variety of other regions of the patient for additional types of therapy.

The control system 12 employs patient data for a patient 18, such as can be stored in an associated memory device 22 (e.g., locally or remotely). The patient data includes electrical data 24 that represents electrical information for a plurality of points, each of which is indexed or otherwise programmatically associated with (e.g., linked to) an anatomical geometry of the patient 18. In the example of FIG. 1, the electrical data 24 is obtained via a sensor array 26, which can be disposed on the body surface non-invasively or be invasively positioned inside the patient 18. For example, the sensor array 26 can correspond to a plurality of electrode sensors, such as a vest or electrode carrying apparatus, that are placed on a body surface of the patient 18 and which are configured to monitor electrical activity of one or more organs of the patient 18, such as the heart of the patient 18.

In some examples, the sensor array 26 can correspond to a predetermined zone of the patient's body surface that has been determined to be a surrogate that maps deterministically to one or more specific regions of interest of the organ of the patient 18, as disclosed herein.

The patient electrical data 24 can be raw data, such as has been collected from the sensor array 26 (e.g., an arrangement of body surface electrodes, an electrophysiology mapping catheter) or other means that can be utilized to acquire electrophysiology data for a selected region of the patient 18 (e.g., a segment of an organ, such as the heart). Additionally or alternatively, the electrical data 24 can correspond to processed data, such as can be processed data, such as can be sampled and filtered to provide electrophysiology information for the selected region of the patient 18.

The patient data can also include geometry data 28, such as can be embodied as a geometry model for a three-dimensional region of anatomy of the patient 18. The model can correspond to an image of the organ of the patient 18, such as obtained via any of a variety of imaging methods. As another example, the model can be a generic model, or can be a modified version of a generic model that is adjusted for the patient 18 based on dimensions determined for a patient's organ. For instance, a generic model can be modified based on measurements and/or imaging data for the patient 18, such as disclosed herein. The geometry data 28 can correspond to a surface of model of an entire organ of the patient 18, such as the heart, which can be graphically rendered in an output display as a two- or three-dimensional representation.

In some examples, the therapy system 14 can be configured to deliver CRT. By way of example, non-invasive electrophysiological mapping (e.g., electrocardiographic (EC) mapping for the heart) can be performed on a body surface of the patient 18 to generate the electrical data 24. This technique can generate electrophysiological data by combining body surface electrical measurements from the sensor array 16 with patient geometry information through an inverse method programmed to reconstruct the electrical activity for a predetermined surface region of the heart of the patient 18. Thus, the results of the inverse method can provide the corresponding electrical data 24 that is registered with the patient's own geometry, such as can be represented in the geometry data 28. Thus, the electrical data 24 can represent reconstructed electrical signals (e.g., time-based electrical potentials) for each of the plurality of points on a cardiac envelope concurrently as a function of time, such as an epicardial surface, endocardial surface or other envelope.

In another example, the sensor array 26 can be implemented as a contact or non-contact electrophysiology catheter can be placed in heart of the patient 18 and collect electrophysiology data at a plurality of spatial locations over time, such as during a number of one or more cardiac intervals. Such data can be spatially and temporarily aggregated in conjunction with image data for the heart of the patient 18 to provide the electrical data 24 for corresponding regions of the heart of the patient 18. Alternatively, the sensor array 26 can be implemented as other devices (e.g., catheters or patches) that can be placed on or near the heart of the patient 18, endocardially and/or epicardially, such as during open chest and minimally invasive procedures, to record electrical activity data, which can be mapped to a representation of the heart of the patient 18 to provide similar corresponding electrical data 24.

Those skilled in the art will understand and appreciate that the system 10 is equally applicable to patient electrical data 24 that can be gathered and/or derived by any of these or other approaches, which may be invasive or non-invasive. Additionally, it will be understood and appreciated that the electrical data 24 can be provided in any form and converted into an appropriate form for processing in the system 10.

As mentioned above, the system 10 also employs geometry data 28, such as can represent a predetermined surface region of an anatomical structure, which can be a generic structure or be specific for the patient 18. For example, the geometry data 28 can correspond to a patient-specific representation of a surface of an organ or other structure to which patient electroanatomical data has been registered. For instance, the geometry data 28 may include a graphical representation of a region of the organ of the patient 18, such as can be generated by appropriate image processing of image data acquired for the patient 18. Such image processing can include extraction and segmentation of an organ from a digital image set. The segmented image data thus can be converted into a two-dimensional or three-dimensional graphical representation of a surface region of the organ. Alternatively, the patient geometry data 28 can correspond to a mathematical model, such as can be constructed based on image data for the organ of the patient 18. Appropriate anatomical or other fiducial landmarks can be associated with the organ represented by the anatomical data for the organ to facilitate subsequent processing and visualization in the system 10.

As another example, the geometry data 28 can correspond to or be associated with a generic model of the respective organ. The generic model can correspond to a model that is associated with general physical attributes of the patient 18, such as height, weight, age, and/or other characteristics of the patient 18. The control system 12 can thus map the electrical data 24 to the generic model, such as disclosed herein. As another example, simplified image data can be obtained for the organ of the patient 18, such as can be implemented to modify the generic model to better represent the actual organ of the patient 18. Thus, the control system 12 can map the electrical data 24 onto the adjusted generic model corresponding to the organ of the patient 18, such as disclosed herein. In still other examples where the sensor array 26 include a zone of electrodes known a priori to map to predetermined region of interest of the organ, mapping and imaging can be omitted altogether to further simplify the computations, and still provide useful diagnostic information for the predetermined ROI of the patient's organ. Additionally or alternatively, the electrical signals sensed from the predetermined zone of electrodes can be mapped as reconstructed electrical signals onto a predefined region of interest of a cardiac envelope by employing a predetermined inverse solution that has been derived a priori to perform such mapping from the predetermined zone to the predefined region of interest in the absence of additional imaging.

Figure 2:
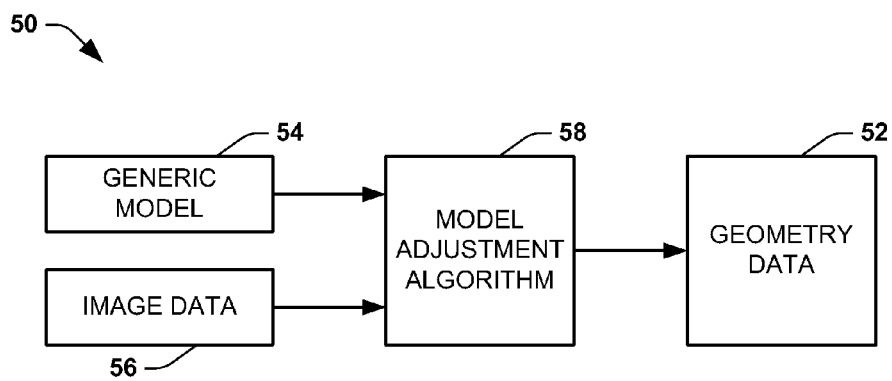
FIG. 2 depicts an example of a system for generating geometry data associated with at least one internal anatomical structure of a patient.

FIG. 2 depicts an example of a system 50 that can be implemented for generating geometry data 52 associated with at least one internal anatomical structure of a patient. The geometry data 52 can correspond to the geometry data 28 in the example of FIG. 1. Therefore, reference is to be made to the example of FIG. 1 in the following description of the example of FIG. 2 for additional context.

The system 50 demonstrates a generic model 54 that can correspond to dimensional data associated with a model of the organ, such as a heart or brain. The generic model 54 can be a model that is not specific to the patient 18, but can correspond to a model having general features for the respective organ applicable to any or a subset of patient. For example, the generic model 54 can be selected from a plurality of models, each being associated with general physical attributes of different patients, such as may vary according to height, weight, age, and/or other characteristics of the patient 18. The generic model 54 can include dimensions associated with features of the respective organ for which the therapy is associated.

The system 50 also demonstrates image data 56, such as can be obtained for the patient including the organ for which therapy is to be applied. The image data 56 can correspond to data resulting from any of a variety of invasive and/or non-invasive imaging techniques. As an example, the image data 56 can be generated from image data that is acquired using nearly any imaging modality. Examples of simplified imaging modalities include ultrasound, X-ray, venography, fluoroscopy and the like. Where available, the image data can be obtained by using other more complex imaging modalities, such as computed tomography (CT), 3D Rotational angiography (3DRA), magnetic resonance imaging (MRI), and positron emission tomography (PET). These complex imaging modalities thus can be utilized to generate three-dimensional geometry data for the patient's heart, such as for use in reconstructing electrical signals on a cardiac envelope as disclosed herein.

In the example of simplified imaging modalities, since the purpose of the image data may not be full registration of the sensor array and patient geometry for the organ for reconstruction purposes, but instead to determine certain dimensional information, image data obtained from the simplified imaging modalities can be used at a considerable cost savings. For example, the image data 56 can include a set of data corresponding to basic or a small set of dimensional information associated with a periphery of the organ, such as points along extrema of the organ. As used herein, the term "extrema" refers to a point on a plane at an extreme distance from each other along a given axis extending through the anatomical structure (e.g., heart). Because the more simplistic imaging of the organ can be implemented to obtain no more information than dimensions associated with peripheral fiducial points or the extrema of the organ, the imaging technique and processing thereof can be affected in a much more rapid and/or less computational manner. It will be understood and appreciated by those skilled in the art that the type of imaging modality of the image data 56 can vary according to the purpose or purposes of the image data 56. Additionally, it is conceivable that one or more image sets can be acquired by one or more imaging modalities, each of which can be stored as the patient geometry data 28.

The system 50 can include a model adjustment algorithm 58 that is programmed to adjust the model 54 based on the dimensional information to provide the geometry data 52. The geometry data 52 can include a modified model of the organ. The modified model thus can correspond to version of the model that has been customized for a patient based on dimensions of the patient's organ. The modified model can be provided to apply an inverse algorithm for reconstructing electrograms on a cardiac envelope, such as disclosed herein.

Figure 3:
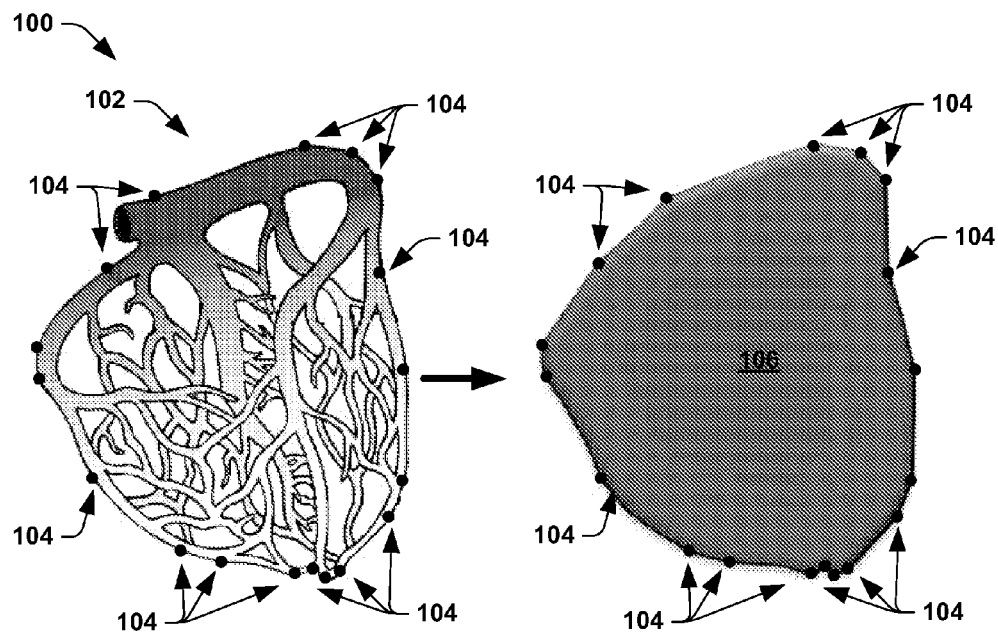
FIG. 3 depicts an example diagram of an imaging technique to obtain dimensions of an organ.

FIG. 3 depicts an example diagram 100 of an imaging technique to obtain dimensions of an organ such as the heart. The technique can be implemented to obtain the image data 56 in the example of FIG. 2. Therefore, reference can be made to the example of FIGS. 1 and 2 in the following description of the example of FIG. 3. In addition, in the example of FIG. 3, the imaging technique includes obtaining a venogram of the heart of the patient 18. However, it is to be understood that any of a variety of different manners of imaging can be implemented in the imaging technique to image a variety of different types of organs.

The diagram 100 demonstrates a venogram image 102 of the veins surrounding the heart of the patient 18. The venogram image 102 can be obtained, for example, based on injecting a radioactive dye into the bloodstream of the patient 18 and obtaining a radiography image of the heart. Upon obtaining the venogram image 102, a processing system (e.g., included in the control system 12 or provided by external imaging equipment) can designate a plurality of fiducial points 104 along the periphery of the venogram image 102. As an example, the fiducial points 104 can be substantially evenly spaced in two or three dimensions along the periphery of the venogram image 102. As another example, the fiducial points 104 can be designated at extrema around the periphery of the venogram image 102 at a predetermined number of axes through the venogram image 102, such as to define boundaries of the venogram 102. As yet another example, the fiducial points 104 can be designated to identify specific regions of interest of the heart, such as scar tissue or specific regions of interest for the heart.

The diagram 100 thus also demonstrates a simplified image representation 106 that can be generated for the heart. The simplified image 106 of the heart can thus correspond to a featureless three-dimensional representation of the outer dimensions of the heart. For example, the associated processor can be configured to connect the fiducial points 104 to obtain the simplified image 106 of the heart in three dimensions. Accordingly, the image data 56 can correspond to the simplified image 106 of the heart. As another example, the associated processor could be configured to simply calculate distances between the fiducial points 104. Therefore, in this example, the simplified image 106 of the heart is not generated, but is instead demonstrated by a set of dimensions associated with each of the fiducial points 104, such as relative to each other or to neighboring fiducial points 104. Accordingly, the image data 56 can correspond to the set of dimensions based on the identified the fiducial points 104.

Figure 4:
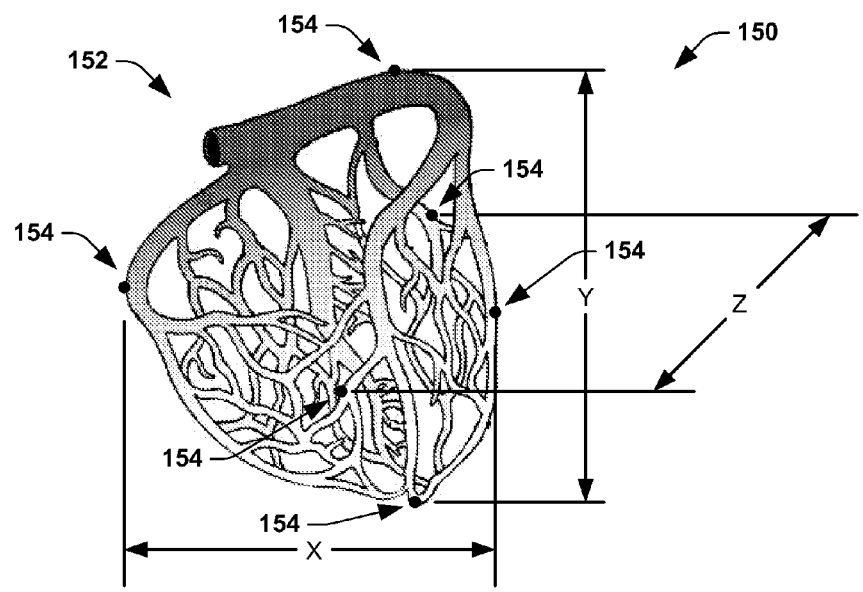
FIG. 4 depicts another example diagram of an imaging technique to obtain dimensions of an organ.

FIG. 4 depicts another example diagram 150 of an imaging technique to obtain dimensions for providing geometry of an organ. The technique can be implemented to obtain the image data 56 in the example of FIG. 2. Therefore, reference is to be made to the example of FIGS. 1 and 2 in the following description of the example of FIG. 4. In addition, in the example of FIG. 4, the imaging technique includes obtaining a venogram of the heart of the patient 18. However, it is to be understood that any of a variety of different manners of imaging can be implemented in the imaging technique to image a variety of different types of organs.

Figure 5:
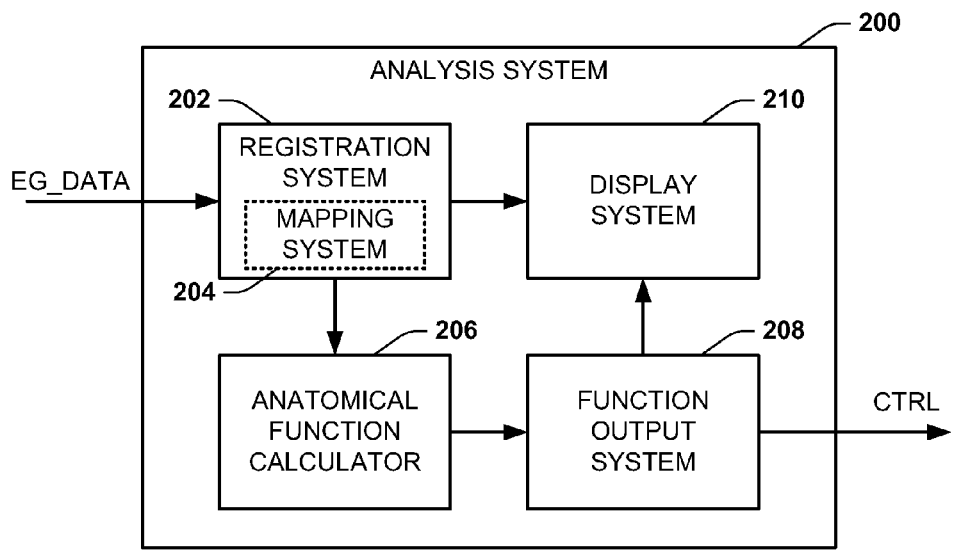
FIG. 5 depicts an example of an analysis system for providing therapy for a patient.

In the example of FIG. 5, the image 150 demonstrates a venogram image 152 of the veins surrounding the heart of the patient 18. Upon obtaining the venogram image 152, a processing system (e.g., included in the control system 12 or provided by external imaging equipment) can designate extrema points 154 at the periphery of the venogram image 102 in two or three orthogonal axes. The extrema points 154 of the venogram image 152 can include points at the furthest extensions in height, width, and depth in a Cartesian coordinate system.

For example, by designating the extrema points 154 of the venogram 152, the associated processor can calculate extrema dimensions in the X, Y, and Z Cartesian coordinate axes. The extrema dimensions in the X, Y, and Z Cartesian coordinate axes can thus correspond to simplified image data associated with the heart of the patient 18 in two or three orthogonal axes. Accordingly, the image data 56 can correspond to extrema dimensions of the heart in the X, Y, and Z Cartesian coordinate axes. Other coordinate systems can be used.

Referring back to the example of FIG. 2, the model adjustment algorithm 58 can be configured to modify the generic model 54 of the internal anatomical structure based on dimensions of the internal anatomical structure of the patient 18 provided in the image data 56. For example, the model adjustment algorithm 58 can be configured to stretch or contract the features of the generic model 54 based on the dimensions associated with the simplified image 106, as provided in the example of FIG. 3, or based on the extrema dimensions of the internal anatomical structure (e.g., heart) in the X, Y, and/or Z Cartesian coordinate axes, as provided in the example of FIG. 4. Accordingly, the model adjustment algorithm 58 can generate an adjusted model that is associated with the actual dimensions of the internal anatomical structure of the patient 18. The adjusted model is thus saved as the geometry data 52 that can be implemented for analysis, as disclosed herein. For example, the geometry data 52 can be generated as a graphical or array representation of the internal anatomical structure of the patient 18 based on the model adjustment algorithm 58.

It is to be understood that the generation of the geometry data 52 in the example of FIG. 2 is provided as an example, and that other manners of generating the geometry data 52 can be implemented. For example, the geometry data 52 can be generated absent a generic model 54. As one example, the geometry data 52 can be generated based on raw image data that is obtained via any of a variety of imaging techniques. As another example, the image data 56 that is obtained via simplified imaging techniques, such as described in the examples of FIGS. 3 and 4, may be converted directly into the geometry data 52, and thus may be implemented without modifying a generic model 54. As a result, the geometry data 52 can be a greatly simplified set of data corresponding to the internal anatomical structure of the patient 18 when compared to geometry data used with more complex imaging modalities.

Referring back to the example of FIG. 1, the control system 12 also includes an analysis system 30. The analysis system 30 is configured to analyze the electrical data 24 relative to the geometry data 28 to determine an efficacy of the therapy that is delivered to the patient 18. The analysis can be performed for a given set of electrical data 24 that corresponds to a given one or more values of a therapy parameter, as provided by the therapy system 14, at each of a plurality of iterations of the therapy. For example, upon analyzing the electrical data 24 relative to the geometry data 28 for a given iteration, the analysis system 30 can instruct the parameter controller 20 to change one or more values of the parameter(s) associated with the therapy being delivered to the patient 18. The analysis system 30 can thus monitor differences in the electrical data 24 based on the adjustment to the one or more values of the parameter(s) associated with the therapy being delivered to the patient 18 at a next iteration. As an example, the change to the one or more values of the parameter(s) associated with the therapy can be based on the monitored difference in an observed functional and/or structural characteristic of the organ derived from the electrical data 24. In this way, the change in therapy can be responsive to identified effects of the value(s) of the set of one or more parameters of the therapy in a given iteration. Accordingly, the analysis system 30 can be configured to provide the therapy to the patient 18 in a closed-loop feedback manner.

FIG. 5 depicts an example of an analysis system 200 for providing therapy for a patient. The analysis system 200 can correspond to the analysis system 30 in the example of FIG. 1. Therefore, reference is to be made to the example of FIG. 1 in the following description of the example of FIG. 5.

The analysis system 200 can be programmed to compute an indication corresponding to a biological function of the organ, such as can represent a structural, electrical or a combination of structural and electrical functions. The analysis system 200 can be implemented as computer-executable instructions implemented on a processor running remotely or locally on a computer. A user interface (not shown) can be utilized to activate or otherwise interact with the analysis system 200.

In some examples, the analysis system 200 can calculate an indication of synchrony of a heart of the patient 18. The indication of synchrony can be employed to provide a quantitative measure of synchrony for the heart or a measure of dyssynchrony for the heart or a combination of synchrony and dyssynchrony, such as to provide CRT.

The analysis system 200 can include a registration system 202 that is configured to obtain a set of electrogram data, demonstrated in the example of FIG. 5 as EG_DATA. The set of data EG_DATA can correspond to the electrical data 24 and the geometry data 28, such as accessible from the memory 22 by the analysis system 200. The registration system 202 can thus be configured to register the electrical data 24 to a common coordinate system with the patient geometry data 28. For instance, the electrical data 24 can be stored in a data structure of rows (corresponding to different anatomical points) and columns (corresponding to samples) in which the rows of data have the same index as (or are registered to) respective points residing on patient geometry data 28. Is some examples, the electrical data 24 can correspond to body surface electrical signals that can be individually associated with one or more regions of interest of the internal anatomical structure, such as based on the geometry data 28. Thus, the registration system 202 can correlate the body surface electrical signals with the specific one or more regions of interest of the internal anatomical structure.

As a further example, the registration system 202 can also include a mapping system 204. The mapping system 204 can be configured to register the electrical data 24 onto the geometry data 28 in a manner that is associated with an image of the internal anatomical structure (e.g., the heart or other organ) of the patient 18. In one embodiment, the samples of the electrical data 24 can represent simultaneous information across the entire surface region of the patient's body. The mapping system 204 can reconstruct electrical signals for the internal anatomical structure (e.g., the heart) of the patient 18 based on the EG_DATA. As an example, the electrical data 24 can be mapped to the representation of the organ according to identified anatomical landmarks provided by the geometry data 28. For example, the mapping system 204 can implement the inverse method to reconstruct the electrical activity for a predetermined surface region of the internal anatomical structure of the patient 18. Therefore, the electrical data 24 can be mapped to the specific regions of the internal anatomical structure (e.g., the heart) to identify the electrical activity of the specific regions of the internal anatomical structure.

The analysis system 200 also includes an anatomical function calculator 206 that is configured to calculate at least one function of the internal anatomical structure based on the registration of the electrical data 24 with the geometry data 28. In some examples, the anatomical function calculator 206 can be configured to calculate synchrony of the heart of the patient based on reconstructed electrical signals computed by the mapping system. In other examples, the anatomical function calculator 206 can be configured to calculate synchrony of the heart of the patient directly from the electrical data sensed from a predetermined zone of the patient's body surface that has been determined to be a surrogate for a specific region of interest of the patient's organ (i.e., without having to compute reconstructed electric signals on the patient's organ).

By way of further example, the anatomical function calculator 206 can be programmed to quantify an indication of synchrony based on the one or more temporal characteristics based on the registration of the electrical data 24 with the geometry data 28 over time. By way of further example, the anatomical function calculator 206 can calculate one or more indices such as including a global synchrony index (GSI), an intraventricular conduction index (ICI), a segmental synchrony index (SSI), and/or a late activation index. For instance, the anatomical function calculator 206 can provide a measure of synchrony based upon statistical analysis of activation times for the left ventricle relative to the right ventricle of the heart of the patient 18. An example of calculation of heart synchrony that can be implemented is shown and described in International Application No. PCT/US11/59174, which was filed 3 Nov. 2011, which is incorporated herein by reference.

The computed function of the internal anatomical structure can be provided to a function output system 208 that is configured to arrange the function information into a format suitable for review, such as by a physician or user of the control system 12. The format is provided to a display system 210 that is configured to provide a graphical display of the function of the internal anatomical structure. For example, the display system 210 can include a computer monitor configured to display an image of the internal anatomical structure, as well as the associated characteristics of the respective function(s). The image of the internal anatomical structure can be provided via the registration system 202, such as based on the geometry data 28, and can demonstrate the function on the image in a variety of ways, such as numerically and/or color-coded. For example, the display system 210 can display the function on respective sets of regions of interest of the internal anatomical structure, such as based on the registration of the electrical data 24 to the geometry data 28.

In addition, the function output system 208 can be configured to determine a set of one or more values associated with parameters of the therapy to provide to the parameter controller 20 for administering the therapy to the patient 18 in a next iteration. For example, the function output system 208 can identify an effect of the therapy on the patient 18 at a given iteration based on a given set of value(s) for parameters associated with the therapy. Such effect corresponding to the function of the internal anatomical structure can be saved in a memory, such as the memory 22. The function output system 208 can thus calculate or otherwise identify a change to the value(s) for the parameters for a next iteration to optimize the therapy being delivered to the patient 18 based on the effect of the set of value(s) in a previous iteration, such as by accessing the indication of the function from the memory (e.g., the memory 22). Therefore, in the example of FIG. 5, the function output system 208 provides a signal CTRL to the parameter controller 20 to command the therapy system 14 to administer the therapy to the patient 18 based on the changes to the value(s) identified by the function output system 208. Accordingly, the function output system 208 controls the administration of the therapy to the patient 18 based on the measured electrical data 24 in a closed-loop feedback manner.

As described previously, the electrical data 24 can be ascertained based on monitoring the sensor array 26 positioned at predetermined zones that can correspond to specific regions of interest of the internal anatomical structure. For example, it can be a priori ascertained that collecting electrical data from predetermined regions on the body surface of the patient 18 can correspond to electrical information associated with predetermined regions of the heart, such as the left and right ventricles. Therefore, the sensor array 26 can be provided in a manner that is specific to gathering electrical data 24 that is pertinent to the specific type of information necessary to administer the respective therapy to the patient 18.

Figure 6:
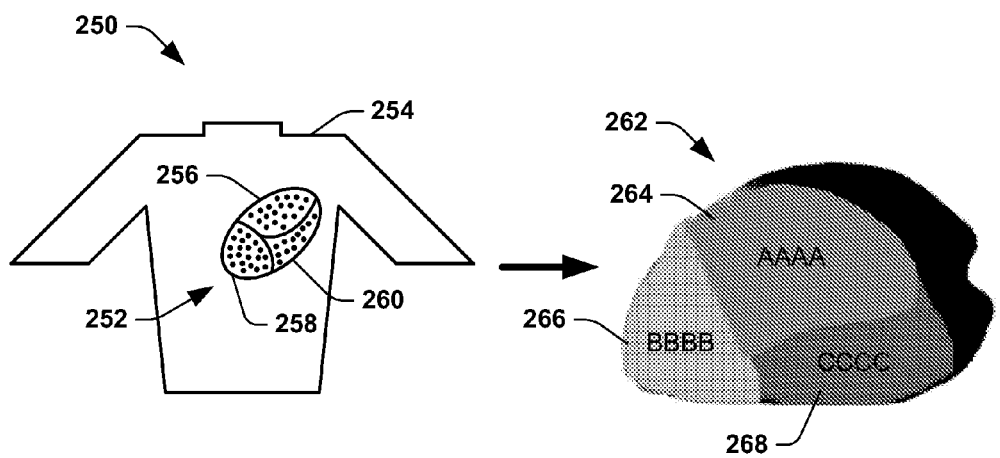
FIG. 6 depicts an example diagram of collecting electrical data for providing therapy for a patient.

FIG. 6 depicts an example diagram 250 that can be utilized for collecting electrical data for a patient. The approach can be utilized in connection with providing a therapy, such as in a closed loop manner as disclosed herein, as well as solely for diagnostic purposes separate from therapy delivery. The diagram 250 can correspond to collecting the electrical data 24 of the patient 18 in the example of FIG. 1. Reference can be made to the example of FIG. 1 in the following description of the example of FIG. 6 for additional context for how it may be utilized as part of a system or method to deliver therapy.

The diagram 250 demonstrates a sensor array 252 that has been placed on a body surface of a patient 254. The sensor array 252 can include an array of sensors (e.g., electrodes) that can contact with the body surface of the patient 254, such that the sensors can each be configured to monitor electrical signals at different predetermined locations on the body surface of the patient 254. The sensor array 252 can correspond to one or more predetermined zones of the patient's body surface. In the example of FIG. 6, the sensor array includes a plurality of discrete, separate zones, including a first zone 256, a second zone 258, and a third zone 260. Each of the separate zones 256, 268, and 260 can correspond to map deterministically to a different specific region of interest on the heart of the patient 254, which can be determined a priori. For example, the sensors in each of the separate zones 256, 268, and 260 can be implemented to collect electrical data of respective corresponding regions of interest of the heart of the patient 254. For example, the sensors of the separate zones 256, 258, and 260 can be associated based on substantially adjacent sensors to correspond to contiguous portions of the internal anatomical structure.

The diagram 250 also demonstrates an image for the heart 262 that includes a plurality of different regions of interest for the heart. In the example of FIG. 6, the image for the heart 262 can represent the left-ventricle of the heart, including a lateral portion 264, an apex portion 266, and a base portion 268. For example, the image for the heart 262 can correspond to a general image model for representing a heart, such as the type typically utilized in electrophysiology studies or as may be selected by a user. As an example, image for the heart 262 can correspond to a graphical representation of a heart, such as a simplified illustration of a heart that has unspecific associated dimensions. As yet another example, the diagram 262 can correspond to an image of the actual heart of the patient 254, such as obtained via a variety of imaging techniques.

In the example of FIG. 6, the first zone 256 of the sensor patch 252 can correspond to monitoring electrical data associated with the lateral portion 264 of the left ventricle of the heart of the patient 254. Similarly, the second zone 258 can correspond to monitoring electrical data associated with the apex portion 266 of the left ventricle of the heart of the patient 254 and the third zone 260 can correspond to monitoring electrical data associated with the base portion 268 of the left ventricle of the heart of the patient 254. The correlation of the zones with the 256, 268, and 260 with the portions 264, 266, and 268 of the left ventricle of the heart can be based on prior collected electrical data from a plurality of patients over respectively applied therapies. For example, correlation data can be collected over the administration of a specific therapy to a plurality of patients to ascertain an associated of the location of the zones 256, 268, and 260 with the specific portions 264, 266, and 268 of the left ventricle of the heart of patients. Such correlation can account for physical attributes of the patients, such as to ascertain a location of placement of the sensor patch 252 on the body surface of the patient 254 based on the patient's respective physical attributes. Such placement can also be based on implementing an imaging apparatus, such as X-ray imaging devices to guide the sensor patch 252 to the appropriate portion of the body surface of the patient 254.

For example, such a priori knowledge of the correlation of zones with regions of interest of the internal anatomical structure can be implemented to develop a variety of different sensor array devices for collecting electrical data associated with the internal anatomical structure of patients, such as similar to the sensor patch 252. For example, the correlation of zones with regions of interest can be implemented to provide sensor patches in one or more pieces having shapes that can conform to external anatomical portions of a given patient, such as arms, legs, and the head, as well as conforming to the left and right sides of the patients. Other types of sensor array devices can be implemented, such as bands, vests, and other worn devices that can have array zones of sensors that correspond to specific known regions of interest of the internal anatomical structure or structures of a given patient.

In the example of FIG. 6, based on the correlation of the zones 256, 268, and 260 with the portions 264, 266, and 268 of the left ventricle of the heart, the collected electrical data can be correlated directly to the specific portions 264, 266, and 268 of the left ventricle or other regions of interest for the heart such as to provide accurate calculation of the function (e.g., synchrony) of the heart. For example, the registration system 202 can be configured to associate the electrical data 24 of the respective zones 256, 268, and 260 with the portions 264, 266, and 268 of the left ventricle of the heart. In the example of FIG. 6, the diagram 262 is depicted to include data "AAAA" associated with the lateral portion 264, such as collected by the sensors in the zone 256, data "BBBB" associated with the apex portion 266, such as collected by the sensors in the zone 258, and data "CCCC" associated with the base portion 268, such as collected by the sensors in the zone 260. A further example of correlating electrical data to portions of an internal anatomical structure that can be implemented is shown and described in Provisional Application No. 61/546,083, which was filed 12 Oct. 2011, which is incorporated herein by reference.

Therefore, the anatomical function calculator 206 can determine the function (e.g., synchrony) of the heart based at least in part on the correlation of the zones 256, 268, and 260 with the portions 264, 266, and 268 of the left ventricle of the heart. Furthermore, the function output system 208 can implement the correlation demonstrated in the diagram 262, such as in providing commands to the parameter controller 20 via the signal CTRL, and by providing the data necessary to display of such information via the display system 210. Accordingly, a physician or user of the control system 12 can ascertain the data associated with each of the portions 264, 266, and 268 of the left ventricle of the heart of the patient 254.

It is to be understood and appreciated that the correlation of predetermined zones to specific regions of interest of an internal anatomical structure is not limited to portions of the heart, as demonstrated in the example of FIG. 6. Thus, electrical data of any of a variety of anatomical structures can be obtained from known regions of interest in a manner similar to as described herein.

Figure 7:
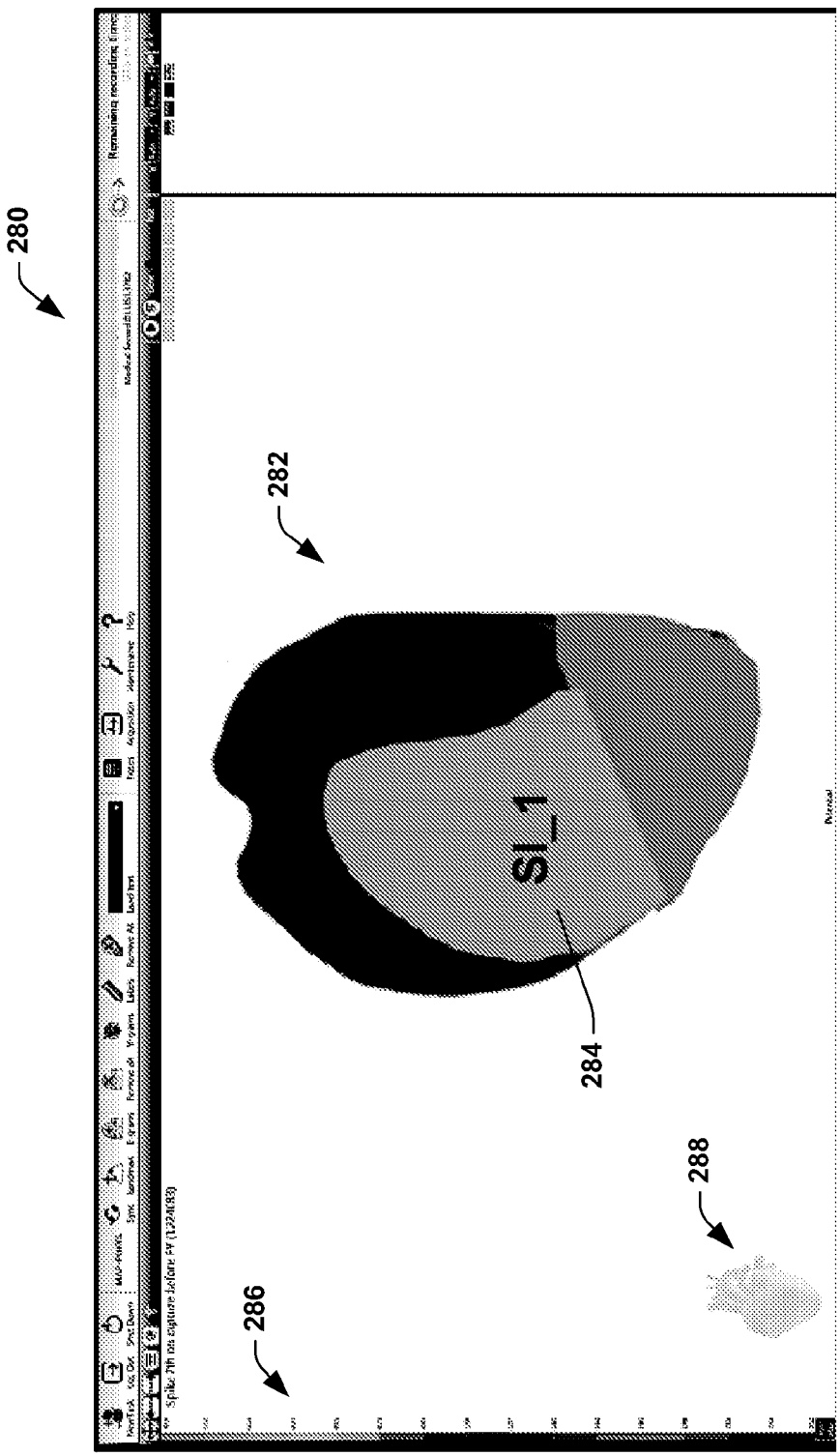
FIG. 7 depicts an example of a display that can be generated demonstrating an indication of heart function for a predetermined region of interest.

As a further example, FIG. 7 depicts an example of a display 280 (e.g., a graphical user interface) that can be generated by systems and methods disclosed herein. The display 280 includes a graphical representation of a heart 282 that has been divided into a plurality of regions of possible interest. In the example of FIG. 7, a value (SI_1), such as a index that represents synchrony for a given region of interest 284 is superimposed on the which a potential map has been displayed corresponding to reconstructed electrical signals at a selected time. The value could be other indicators of cardiac function that may be computed for each separate region of interest directly from the sensed electrical data from a predetermined zone of electrodes as disclosed herein. Additionally or alternatively, the representation of a heart 282 can include color codes, which are specified by a color scale 286 to identify the computed indication of cardiac function. Each such indication of cardiac function, for this example, can be computed directly from the electrical data sensed from a predetermined body surface zone without requiring mapping or reconstruction of electrical signals on to the organ. The display 280 can also include a heart GUI element 288 that represents a user-adjustable orientation of the heart 282.

Figure 8:
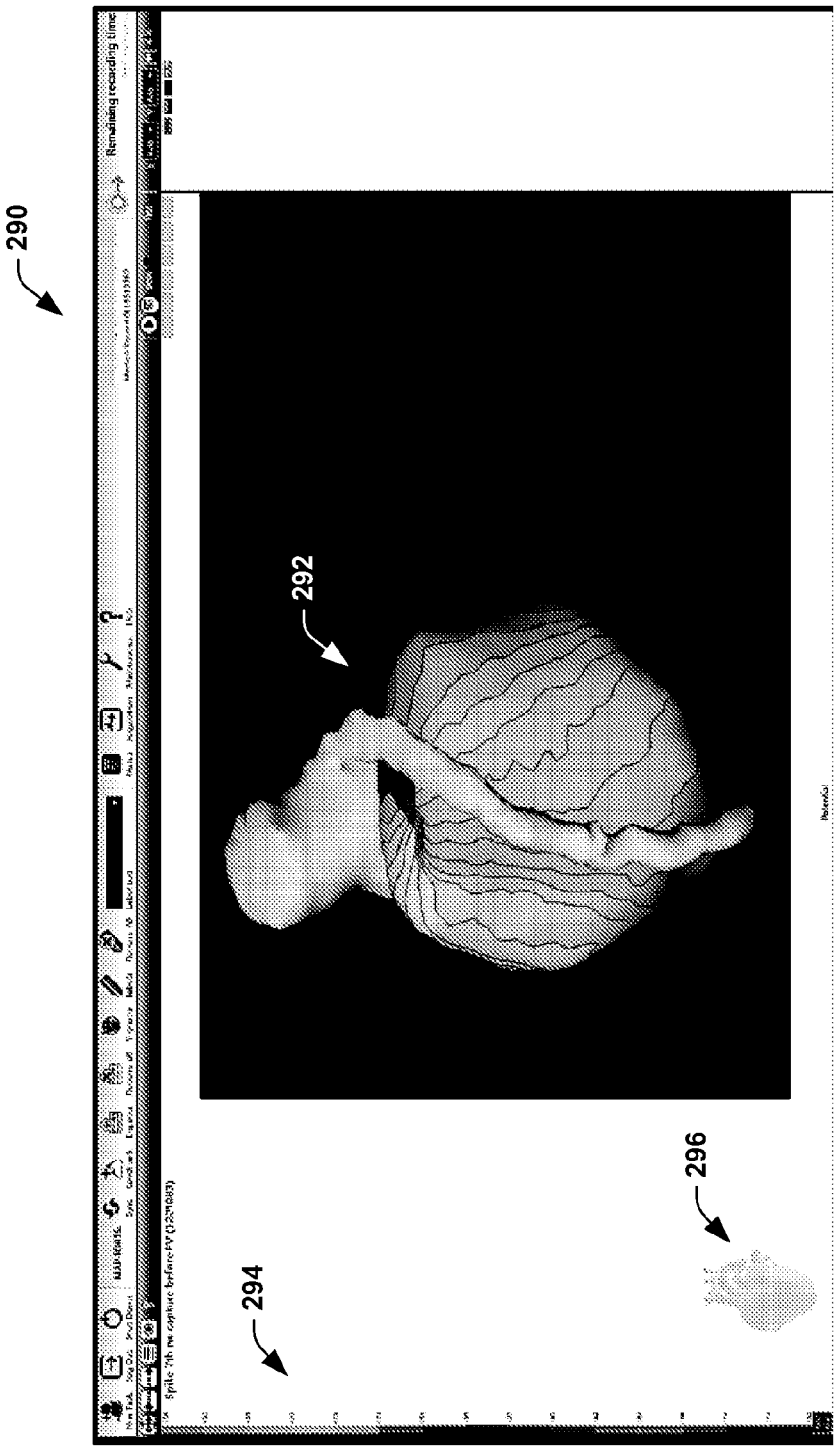
FIG. 8 depicts an example of another display that can be generated demonstrating an indication of heart function for a patient's heart.

FIG. 8 depicts an example of a display 290 (e.g., a graphical user interface) that can be generated by systems and methods disclosed herein. In the example of FIG. 8, the display includes a graphical representation of a cardiac map 292 that includes reconstructed electrical activity, such as can be generated using simplified imaging techniques disclosed herein. The cardiac function information provided in the map 292 can include electrograms that can change over time, activation maps, depolarization maps, synchrony maps and the like, which can be derived from electrical signals obtained from a sensor array and based on geometry data. The cardiac function information can be color coded according to a scale 294. A user can also change the orientation of cardiac map via a user interface element 296.

Figure 9:
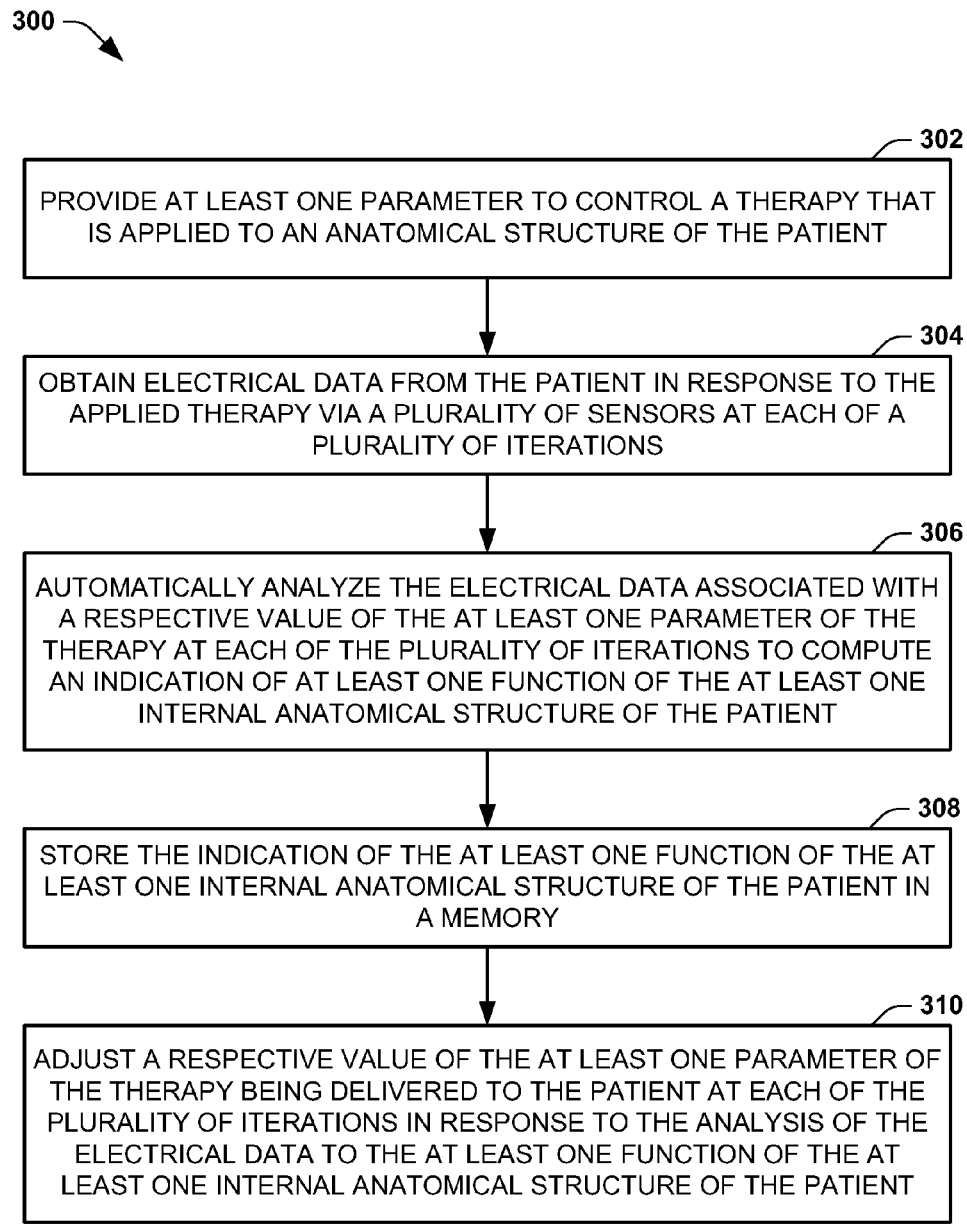
FIG. 9 depicts an example of a flow diagram illustrating an example of a method for providing therapy for a patient.
Figure 10:
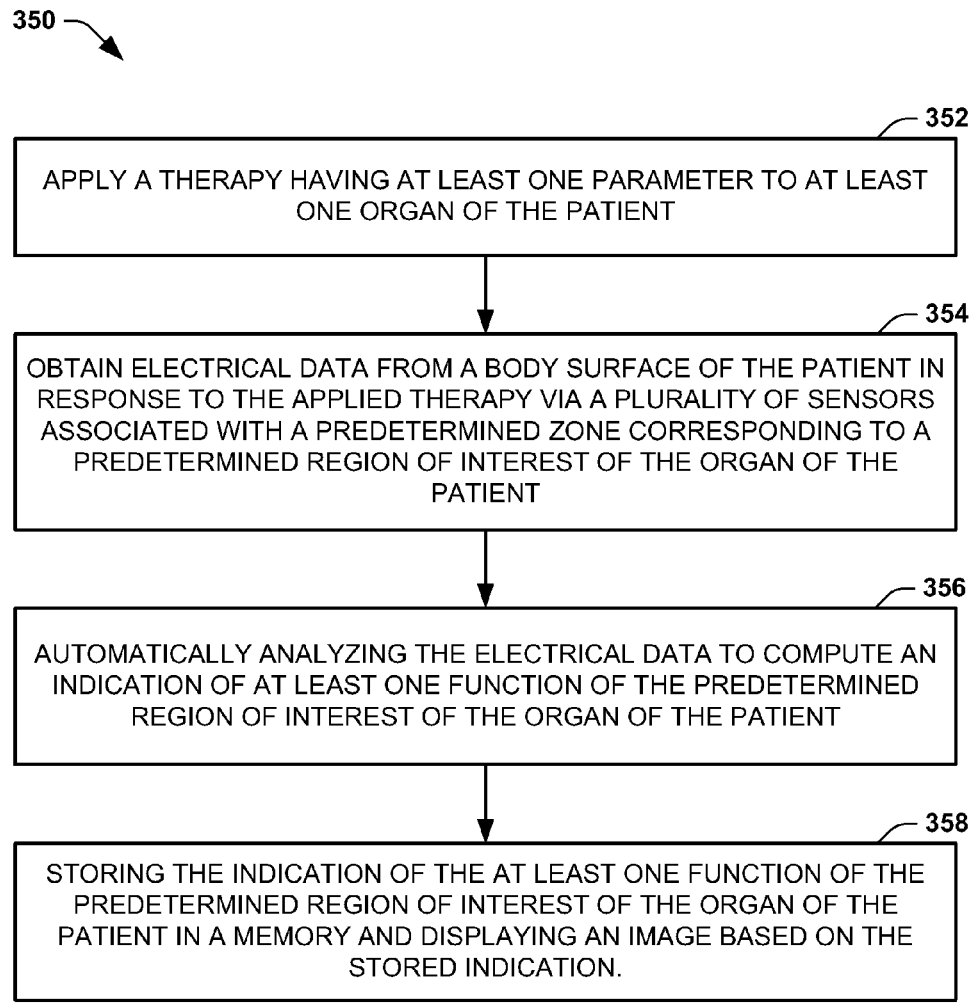
FIG. 10 depicts another example of a flow diagram illustrating an example of a method for providing therapy for a patient.
Figure 11:
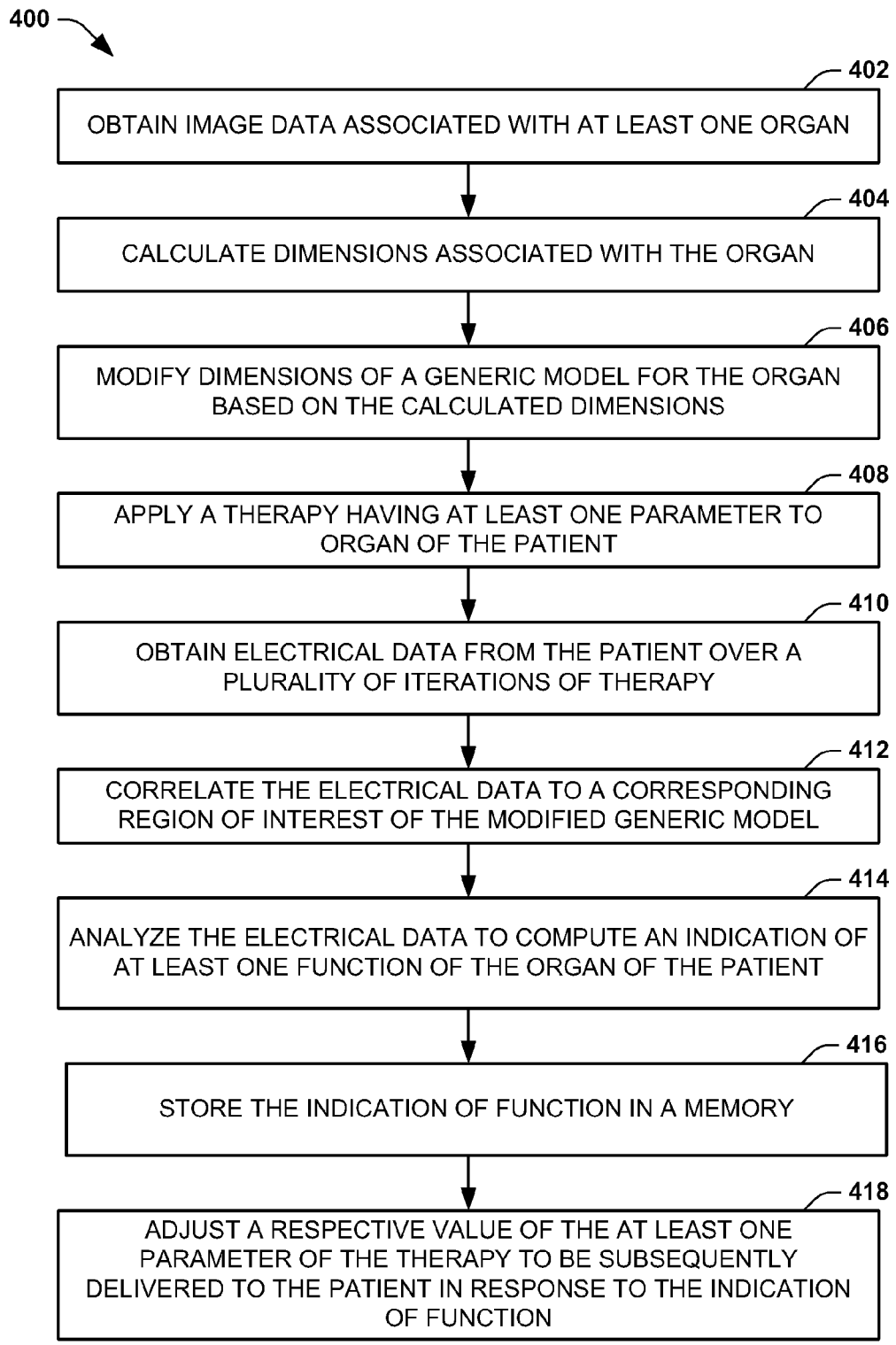
FIG. 11 depicts yet an example of a flow diagram illustrating an example of a method for providing therapy for a patient.

In view of the foregoing structural and functional features described above, methodologies in accordance with various aspects of the present invention will be better appreciated with reference to FIGS. 9-11. While, for purposes of simplicity of explanation, the methodologies of FIG. 9-11 are shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a methodology in accordance with an aspect of the present invention.

FIG. 9 depicts an example of a flow diagram 300 illustrating an example of a method for providing therapy for a patient. At 302, a therapy having at least one parameter is applied to at least one internal anatomical structure of the patient. As an example, the therapy can be CRT that is applied to the heart of the patient. At 304, electrical data is obtained from the patient in response to the applied therapy via a plurality of sensors at each of a plurality of iterations. The electrical data can be obtained from electrode sensors, such as positioned at predetermined zones on a body surface of the patient that each correspond to specific regions of interest of the internal anatomical structure of the patient.

At 306, the electrical data associated with a respective value of the at least one parameter of the therapy is automatically analyzed at each of the plurality of iterations to compute an indication of at least one function of the at least one internal anatomical structure of the patient. The function can be synchrony of the heart, such as in CRT. The analysis can occur based on registration of the electrical data with geometry data associated with the internal anatomical structure. The geometry data can be generated based on providing simplified image data associated with the internal anatomical structure, such as to ascertain dimensions associated with the internal anatomical structure. The dimensions can thus be implemented to modify a generic model of the internal anatomical structure.

At 308, the indication of the at least one function of the at least one internal anatomical structure of the patient in stored in a memory. The memory can be the same memory that stores electrical data and/or geometry data associated with the patient. At 310, a respective value of the at least one parameter of the therapy being delivered to the patient is adjusted at each of the plurality of iterations in response to the analysis of the electrical data to the at least one function of the at least one internal anatomical structure of the patient. The therapy is thus delivered to the patient in a closed-loop feedback manner, such that the therapy is adjusted based on the results of the therapy at a previous iteration.

FIG. 10 depicts another example of a flow diagram 350 illustrating an example of a method that can be used for diagnostic purposes as well as providing therapy for a patient. At 352, a therapy having at least one parameter can be applied to at least one organ of the patient. As an example, the therapy can be CRT that is applied to the heart of the patient. In other examples the method 350 can be performed in the absence of delivering therapy to the patient. At 354, electrical data is obtained from a body surface of the patient in response to the applied therapy via a plurality of sensors associated with a predetermined zone corresponding to a predetermined region of interest of the organ of the patient. The electrical data can be obtained from electrode sensors.

At 356, the electrical data is automatically analyzed to compute an indication of at least one function of the predetermined region of interest of the organ of the patient. The function can be synchrony of the heart, such as for use in CRT. The analysis can occur directly from the electrical signals obtained for the predetermined zone since such signals map deterministically to a predefined region of interest of the organ (e.g., a cardiac segment). In other examples, the analysis can include mapping the electrical data onto the predefined region of interest. Such mapping can be performed based on applying an inverse algorithm programmed for mapping the electrical signals from the predetermine zone onto reconstructed electrical signals at points in the predefined region of interest of the organ without image-based geometry data. In other examples, the mapping can be performed based on registration of the electrical data with geometry data associated with the organ, such as may be obtained a priori for mapping electrical signals from a predetermined body surface zone to a predefined region of interest of the patient's organ. In other examples, the geometry data can be generated based on providing simplified image data associated with the organ, such as to ascertain dimensions associated with the internal anatomical structure. The dimensions can thus be implemented to modify a generic model of the internal anatomical structure, and the inverse algorithm can be applied to the modified model to provide the reconstructed electrical signals on the predefined region of interest of the organ.

At 358, the indication of the at least one function of the predetermined region of interest of the at least one internal anatomical structure of the patient is stored in a memory. The memory can be the same memory that stores electrical data and/or geometry data associated with the patient. In some examples, the indication of function can be displayed for diagnostic purposes, which can be a value (e.g., indicating a synchrony index) and/or as a value superimposed on an image, such as demonstrated in FIG. 7. In other examples, additionally or alternatively, a respective value of at least one parameter of the therapy being delivered to the patient can be adjusted at each of a plurality of iterations in response to analysis of the electrical data to the at least one function of the at least one internal anatomical structure of the patient. Therefore, the therapy can thus be delivered to the patient in a closed-loop feedback manner, such that the therapy is adjusted based on the results of the therapy at a previous iteration.

FIG. 11 depicts yet an example of a flow diagram 400 illustrating an example of a method for providing therapy for a patient. At 402, image data associated with at least one internal anatomical structure of the patient is obtained. The image data can correspond to ultrasound, computed tomography (CT), 3D Rotational angiography (3DRA), magnetic resonance imaging (MRI), X-ray, positron emission tomography (PET), venography to obtain dimensions associated with the internal anatomical structure. At 404, dimensions associated with the at least one internal anatomical structure of the patient are calculated. The dimensions can be associated with respective fiducial points around a periphery of the image of the internal anatomical structure or with extrema of the image of the internal anatomical structure in at least two orthogonal axes. At 406, dimensions of a generic model associated with the at least one internal anatomical structure of the patient are modified based on the calculated dimensions. The dimensions can thus be implemented to stretch or contract the dimensions of the generic model.

At 408, a therapy having at least one parameter is applied to the at least one internal anatomical structure of the patient. As an example, the therapy can be CRT that is applied to the heart of the patient. At 410, electrical data is obtained from the patient in response to the applied therapy via a plurality of sensors at each of a plurality of iterations. The electrical data can be obtained from electrode sensors, such as positioned at predetermined zones on a body surface of the patient that each correspond to specific regions of interest of the internal anatomical structure of the patient. At 412, the electrical data is correlated to a corresponding at least one region of interest of the modified generic model. The correlation can be based on a priori knowledge of an association between the predetermined zones and the regions of interest based on prior therapies administered to a plurality of patients. In other examples the correlation can be performed by mapping electrical data from sensors (e.g., on a body surface) as reconstructed electrical signals on a surface of an organ or other envelope construct associated with the organ based on electrical and geometry obtained for the patient.

At 414, the correlated electrical data associated with a respective value of the at least one parameter of the therapy is automatically analyzed at each of the plurality of iterations to compute an indication of at least one function of the at least one internal anatomical structure of the patient. The analysis can be performed based on the correlation of the electrical data with the specific regions of interest of the internal anatomical structure. At 416, the indication of the at least one function of the at least one internal anatomical structure of the patient is stored in a memory. At 418, a respective value of the at least one parameter of the therapy being delivered to the patient at each of the plurality of iterations is adjusted in response to the analysis of the electrical data to the at least one function of the at least one internal anatomical structure of the patient. The therapy is thus delivered to the patient in a closed-loop feedback manner, such that the therapy is adjusted based on the results of the therapy at a previous iteration. Additionally, the reconstructed electrograms or other relevant data derived therefrom can be displayed as a cardiac map in a display during the delivery of the therapy.

Figure 12:
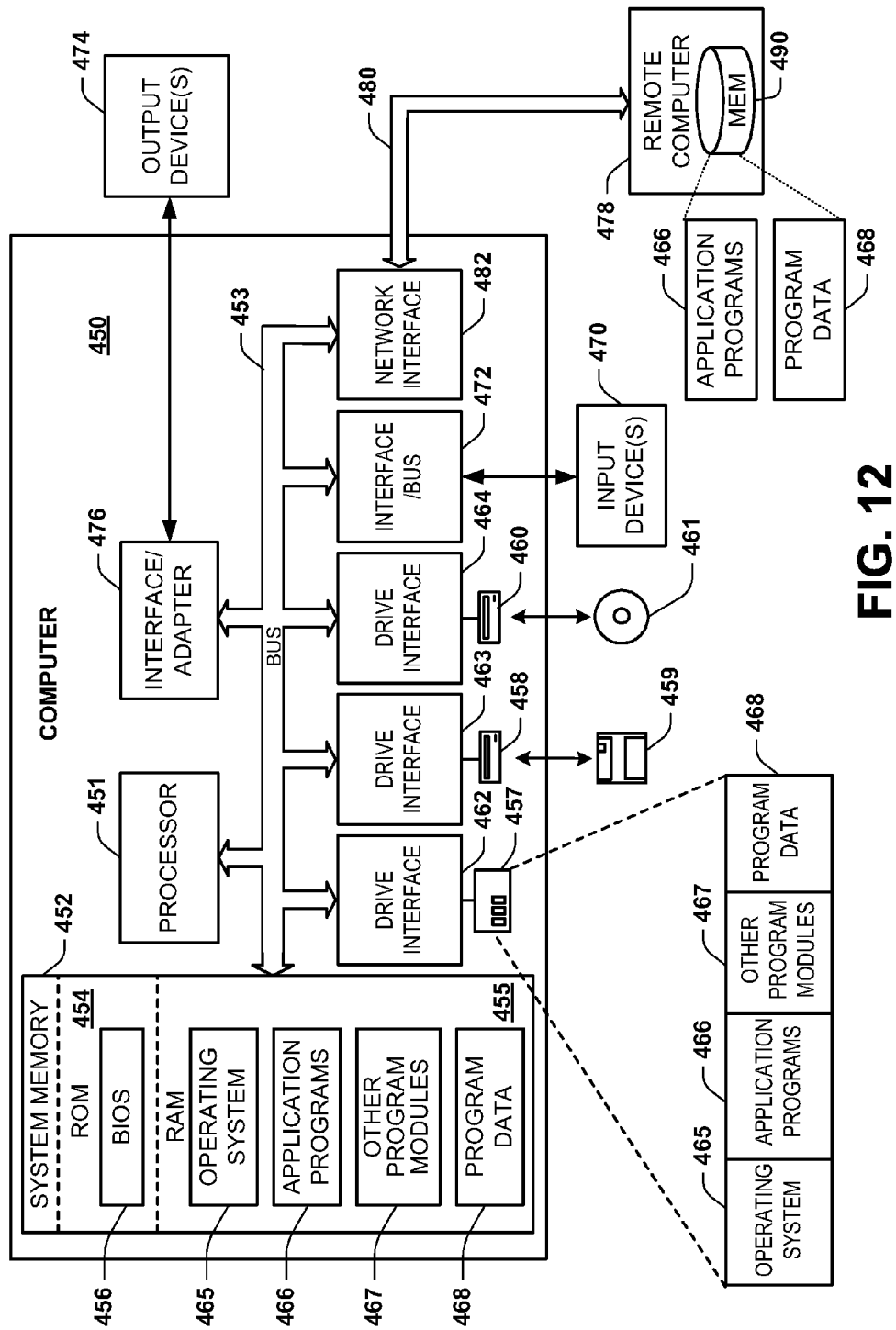
FIG. 12 depicts an example computer system that can be used to perform methods according to an embodiment of the invention.

FIG. 12 depicts an example of a computer system 450 that can be used to perform methods according to an embodiment of the invention, such as including providing therapy to a patient in a closed-loop feedback manner. Computer system 450 can be implemented on one or more general purpose networked computer systems, embedded computer systems, routers, switches, server devices, client devices, various intermediate devices/nodes or stand alone computer systems. Additionally, computer system 450 can be implemented on various mobile clients such as, for example, a personal digital assistant (PDA), laptop computer, pager, and the like, provided it includes sufficient processing capabilities to perform the functions disclosed herein.

Computer system 450 includes processing unit 451, system memory 452, and system bus 453 that couples various system components, including the system memory, to processing unit 451. Dual microprocessors and other multi-processor architectures also can be used as processing unit 451. System bus 453 may be any of several types of bus structure including a memory bus or memory controller, a peripheral bus, and a local bus using any of a variety of bus architectures. System memory 452 includes read only memory (ROM) 454 and random access memory (RAM) 455. A basic input/output system (BIOS) 456 can reside in ROM 454 containing the basic routines that help to transfer information among elements within computer system 450.

Computer system 450 can include a hard disk drive 457, magnetic disk drive 458, e.g., to read from or write to removable disk 459, and an optical disk drive 460, e.g., for reading CD-ROM disk 461 or to read from or write to other optical media. Hard disk drive 457, magnetic disk drive 458, and optical disk drive 460 are connected to system bus 453 by a hard disk drive interface 462, a magnetic disk drive interface 463, and an optical drive interface 464, respectively. The drives and their associated computer-readable media provide nonvolatile storage of data, data structures, and computer-executable instructions for computer system 450. Although the description of computer-readable media above refers to a hard disk, a removable magnetic disk and a CD, other types of media that are readable by a computer, such as magnetic cassettes, flash memory cards, digital video disks and the like, in a variety of forms, may also be used in the operating environment; further, any such media may contain computer-executable instructions for implementing one or more parts of the present invention.

A number of program modules may be stored in drives and RAM 455, including operating system 465, one or more application programs 466, other program modules 467, and program data 468. The application programs and program data can include functions and methods programmed to acquire, process and display electrical data from one or more sensors and to provide for closed loop control for delivery of a therapy (e.g., CRT) to a patient, such as shown and described herein. The application programs and program data can include functions and methods programmed to process data acquired for a patient to facilitate delivering a therapy, such as disclosed herein with respect to FIGS. 1-11.

A user may enter commands and information into computer system 450 through one or more input devices 470, such as a pointing device (e.g., a mouse, touch screen), keyboard, microphone, joystick, game pad, scanner, and the like. For instance, the user can employ input device 470 to edit or modify a domain model. These and other input devices 470 are often connected to processing unit 451 through a corresponding port interface 472 that is coupled to the system bus, but may be connected by other interfaces, such as a parallel port, serial port, or universal serial bus (USB). One or more output devices 474 (e.g., display, a monitor, printer, projector, or other type of displaying device) is also connected to system bus 453 via interface 476, such as a video adapter.

Computer system 450 may operate in a networked environment using logical connections to one or more remote computers, such as remote computer 478. Remote computer 478 may be a workstation, computer system, router, peer device, or other common network node, and typically includes many or all the elements described relative to computer system 450. The logical connections, schematically indicated at 480, can include a local area network (LAN) and a wide area network (WAN).

When used in a LAN networking environment, computer system 450 can be connected to the local network through a network interface or adapter 482. When used in a WAN networking environment, computer system 450 can include a modem, or can be connected to a communications server on the LAN. The modem, which may be internal or external, can be connected to system bus 453 via an appropriate port interface. In a networked environment, application programs 466 or program data 468 depicted relative to computer system 450, or portions thereof, may be stored in a remote memory storage device 490.

What have been described above are examples. It is, of course, not possible to describe every conceivable combination of components or methodologies, but one of ordinary skill in the art will recognize that many further combinations and permutations are possible. Accordingly, the invention is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A non-transitory computer readable medium that, when executed, is configured to implement a method, the method comprising:
   providing at least one parameter to control a therapy that is applied to at least one internal anatomical structure of a patient;
   obtaining electrical data from the patient, including electrical data acquired via a plurality of sensors during each of a plurality of iterations of the therapy, the sensors being distributed across a predetermined spatial zone of a body surface of the patient that provides a surrogate that maps deterministically to at least one predetermined region of interest of the at least one internal anatomical structure;

automatically analyzing the electrical data associated with a respective value of the at least one parameter of the therapy at each of the plurality of iterations of the applied therapy to compute an indication of at least one function of the at least one internal anatomical structure of the patient at each respective iteration of the applied therapy;

storing the indication of the at least one function of the at least one internal anatomical structure of the patient in a memory; and adjusting the at least one parameter of the therapy for delivery in a subsequent one of the plurality of iterations based on the indication of the at least one function.

2. The medium of claim 1, further comprising correlating the electrical data to a corresponding predetermined region of interest of a generic model of the at least one internal anatomical structure.

3. The medium of claim 2, further comprising:
calculating dimensions associated with the at least one internal anatomical structure of the patient; and
modifying the generic model associated with the at least one internal anatomical structure of the patient to provide a modified model based on the calculated dimensions.

4. The medium of claim 3, wherein calculating the dimensions further comprises:
obtaining image data associated with the at least one internal anatomical structure of the patient;
calculating dimensions associated with extrema of the at least one internal anatomical structure of the patient in at least two orthogonal axes based on the image data.

5. The medium of claim 4, wherein calculating the dimensions comprises:
obtaining a plurality of fiducial points at extrema of the at least one internal anatomical structure of the patient based on the image data; and
calculating dimensions between each of the plurality of fiducial points at opposing extrema.

6. The medium of claim 1,
wherein applying the therapy comprises applying cardiac resynchronization therapy (CRT) to a heart of the patient,
wherein automatically analyzing the electrical data comprises automatically analyzing the electrical data associated with a respective value of at least one CRT parameter associated with electrical stimulation of the heart of the patient at each of the plurality of iterations to compute an indication of synchrony associated with the heart of the patient, and
wherein adjusting the at least one CRT parameter comprises adjusting the electrical stimulation being delivered to the heart of the patient at each of the plurality of iterations based on the analysis of the electrical data associated with the synchrony of the heart of the patient.

7. The method of claim 1, wherein the electrical data that is used to compute the at least one function comprises one of (i) body surface electrical signals obtained across the predetermined zone or (ii) reconstructed electrical signals for the at least one predetermined region of interest of the internal anatomical structure derived from the body surface electrical signals distributed across the predetermined zone.

8. A non-transitory computer readable medium that, when executed, is configured to implement a method, the method comprising:
providing at least one parameter to control a therapy that is applied to a heart of a patient;
obtaining electrical data from the patient, including electrical data acquired via a plurality of sensors distributed across a predetermined zone of a body surface of the patient corresponding to at least one predetermined region of interest of the at least one internal anatomical structure during each of a plurality of iterations of the therapy, wherein the predetermined region of interest corresponds to a predetermined region of interest of the heart of the patient;
automatically analyzing the electrical data associated with a respective value of the at least one parameter of the therapy at each of the plurality of iterations of the applied therapy to compute an indication of synchrony for the predetermined region of interest of the heart from the electrical data obtained for the predetermined zone at each respective iteration of the applied therapy;
storing the indication of the synchrony of the predetermined region of interest of the heart in a memory;
adjusting the at least one parameter of the therapy for delivery in a subsequent one of the plurality of iterations based on the indication of the at least one function; and
displaying the computed indication of synchrony on an image of the heart in area of the heart corresponding to the predetermined region of interest.

9. A non-transitory computer readable medium that, when executed, is configured to implement a method, the method comprising:
providing at least one parameter to control a therapy that is applied to at least one internal anatomical structure of a patient;
obtaining electrical data from the patient, including electrical data acquired via a plurality of sensors during each of a plurality of iterations of the therapy;
correlating the electrical data obtained from the patient to at least one corresponding region of interest of a generic model associated with the at least one internal anatomical structure of the patient;
automatically analyzing the electrical data associated with a respective value of the at least one parameter of the therapy at each of the plurality of iterations of the applied therapy to compute an indication of at least one function of the at least one internal anatomical structure of the patient at each respective iteration of the applied therapy;
storing the indication of the at least one function of the at least one internal anatomical structure of the patient in a memory; and
adjusting the at least one parameter of the therapy for delivery in a subsequent one of the plurality of iterations based on the indication of the at least one function.

10. The medium of claim 9, further comprising:
calculating dimensions associated with the at least one internal anatomical structure of the patient; and
modifying the generic model associated with the at least one internal anatomical structure of the patient based on the calculated dimensions to provide a modified model of the at least one internal anatomical structure, wherein correlating the electrical data further comprises correlating the electrical data obtained from the patient to at least one corresponding region of interest the modified model to provide the correlated data.

11. The medium of claim 10, wherein calculating the dimensions further comprises:
   obtaining image data associated with the at least one internal anatomical structure of the patient; and
   calculating dimensions associated with extrema of the at least one internal anatomical structure of the patient in at least two orthogonal axes based on the image data.

12. The medium of claim 11, wherein obtaining the image data comprises at least one of obtaining at least one X-ray image of the at least one internal anatomical structure of the patient, obtaining a venogram image of the at least one internal anatomical structure of the patient, obtaining a fluoroscopy image of the at least one internal anatomical structure of the patient, or obtaining an ultrasound image of the at least one internal anatomical structure of the patient.

13. The medium of claim 11, wherein modifying the generic model comprises modifying dimensions associated with the generic model in each of the at least two orthogonal axes based on the calculated dimensions in the at least two orthogonal axes.

14. A non-transitory computer readable medium that, when executed, is configured to implement a method, the method comprising:
   providing at least one cardiac resynchronization therapy (CRT) parameter to control a CRT that is applied to a heart of a patient;
   obtaining electrical data from the patient, including electrical data acquired via a plurality of sensors during each of a plurality of iterations of the CRT;
   reconstructing electrical signals on a cardiac envelope of the heart based on the electrical data;
   automatically analyzing the reconstructed electrical signals associated with a respective CRT value of the at least one CRT parameter associated with electrical stimulation of the heart of the patient at each of the plurality of iterations of the applied CRT to compute an indication of synchrony associated with the heart of the patient at each respective iteration of the applied CRT;
   storing the indication of synchrony associated with the heart of the patient in a memory; and
   adjusting the electrical stimulation being delivered to the heart of the patient at each of a plurality of iterations based on the analysis of the electrical data associated with the synchrony of the heart of the patient.

15. The medium of claim 14, wherein reconstructing electrical signals further comprises reconstructing the electrical signals on the cardiac envelope of the heart based on the electrical data and three-dimensional geometry data for the heart of the patient obtained from an imaging modality.

16. A non-transitory computer readable medium that, when executed, is configured to implement a method comprising:
   obtaining electrical data for a predetermined zone of a body surface of a patient, the electrical data obtained for the predetermined zone providing a surrogate that deterministically maps to a predetermined region of interest of an organ of the patient;
   automatically analyzing the electrical data, corresponding to body surface electrical signals obtained for the predetermined zone, to compute an indication of at least one function of the predetermined region of interest of the organ of the patient; and
   storing the indication of the at least one function of the predetermined region of interest of organ of the patient in memory; and
   generating an output to display the stored indication of the at least one function on an image of the organ.

17. The medium of claim 16, wherein the predetermined region of interest corresponds to a predetermined region of interest of a heart of the patient,
   the automatically analyzing further comprising computing an indication of synchrony for the predetermined region of interest of the heart directly from the electrical data obtained for the predetermined zone,
   the directly computed indication of the at least one function being displayed on an image of the heart in area of the heart corresponding to the predetermined region of interest.

18. The medium of claim 16, further comprising correlating the electrical data to a corresponding region of interest of a generic model for the organ of the patient.

19. The medium of claim 16,
   wherein the electrical data includes electrical data obtained for the predetermined zone of the body surface while applying cardiac resynchronization therapy (CRT) to a heart of the patient,
   wherein automatically analyzing the electrical data comprises automatically analyzing the electrical data associated with a respective value of at least one CRT parameter associated with electrical stimulation of the heart at each of a plurality of iterations of the applied CRT to compute an indication of synchrony associated with the heart of the patient, and
   wherein adjusting the at least one CRT parameter comprises adjusting the electrical stimulation being delivered to the heart for at least some of the plurality of iterations of the CRT based on the computed indication of synchrony.

20. The medium of claim 16,
   wherein obtaining the electrical data comprises obtaining the electrical data for the predetermined zone of the body surface at each of a plurality of iterations of a therapy, and
   wherein automatically analyzing the electrical data comprises automatically analyzing the electrical data at each of the plurality of iterations of the therapy,
   the method further comprising adjusting at least one parameter associated with the therapy being delivered to the patient at each of the plurality of iterations in response to analyzing the electrical data from the predetermined region of interest of the organ.

21. The medium of claim 16, wherein obtaining the electrical data comprises obtaining the electrical data from the body surface of the patient at each of a plurality of iterations of an applied therapy via a plurality of adjacent sensors associated with the predetermined zone corresponding to a substantially contiguous region of interest of the organ of the patient.

22. A non-transitory computer readable medium that, when executed, is configured to implement a method comprising:
   obtaining electrical data for a predetermined zone of a body surface of a patient, the electrical data obtained for the predetermined zone deterministically mapping to a predetermined region of interest of an organ of the patient;
   correlating the electrical data to a corresponding region of interest of a generic model for the organ of the patient;
   obtaining image data associated that includes the organ of the patient;
   calculating dimensions associated with the organ of the patient;
   modifying dimensions of the generic model for the organ of the patient based on the calculated dimensions;

automatically analyzing the electrical data to compute an indication of at least one function of the predetermined region of interest of the organ of the patient;

storing the indication of the at least one function of the predetermined region of interest of organ of the patient in memory; and generating an output to display the stored indication of the at least one function on an image of the organ.

23. The medium of claim 22, wherein calculating the dimensions comprises calculating dimensions associated with extrema of the organ of the patient in at least two orthogonal axes.

24. A non-transitory computer readable medium that, when executed, is configured to implement a method comprising:

obtaining electrical data for a predetermined zone of a body surface of a patient, the electrical data obtained for the predetermined zone deterministically mapping to a predetermined region of interest of an organ of the patient;

automatically analyzing the electrical data to compute an indication of at least one function of the predetermined region of interest of the organ of the patient; and storing the indication of the at least one function of the predetermined region of interest of organ of the patient in memory; and generating an output to display the stored indication of the at least one function of the predetermined region of interest of the organ on a corresponding region of interest on a visual representation of the organ.

25. A non-transitory computer readable medium that, when executed, is configured to implement a method comprising:

obtaining electrical data for a predetermined zone of a body surface of a patient, the electrical data obtained for the predetermined zone deterministically mapping to a predetermined region of interest of a heart of the patient;

reconstructing electrical signals on a cardiac envelope of the heart based on the electrical data and a predetermined inverse solution programmed to map electrical activity from the predetermined zone of the body surface to the predetermined region of interest of the heart of the patient;

automatically analyzing the reconstructed electrical signals to compute an indication of at least one function of the predetermined region of interest of the heart of the patient; and storing the indication of the at least one function of the predetermined region of interest of heart of the patient in memory; and generating an output to display the stored indication of the at least one function on an image of the heart.

26. A non-transitory computer readable medium that, when executed, is configured to implement a method, the method comprising:

obtaining image data that includes at least one internal anatomical structure of a patient;

calculating dimensions associated with the at least one internal anatomical structure the patient based on the image data;

modifying dimensions of a generic model one of the at least one internal anatomical structure to provide a modified model based on the calculated dimensions;

delivering a therapy having at least one parameter to treat the at least one internal anatomical structure of the patient, the at least one parameter being variable during each of a plurality of iterations of the therapy;

obtaining electrical data from the patient based on electrical activity detected via a plurality of sensors, the electrical data including electrical activity detected in response to the therapy delivered at each of the plurality of iterations of the therapy;

correlating the electrical data to a corresponding region of interest of the modified model;

automatically analyzing the correlated electrical data obtained for a respective value of the at least one parameter of the therapy at each of the plurality of iterations of the therapy to compute an indication of at least one function of the at least one internal anatomical structure of the patient at each of the plurality of iterations of the therapy;

storing the indication of the at least one function of the at least one internal anatomical structure of the patient in memory; and adjusting the at least one parameter of the therapy being delivered to the patient for a given one of the plurality of iterations in response to the computed indication of at least one function from another one of the plurality of iterations.

27. The medium of claim 26, wherein calculating the dimensions comprises calculating dimensions associated with extrema of the at least one internal anatomical structure of the patient in at least two orthogonal axes.

28. The medium of claim 27, wherein modifying the generic model comprises modifying dimensions associated with the generic model in each of the at least two orthogonal axes based on the calculated dimensions in the at least two orthogonal axes.

29. The medium of claim 26, wherein calculating the dimensions comprises:

obtaining a plurality of fiducial points associated with extrema of the at least one internal anatomical structure of the patient; and calculating dimensions of the at least one internal anatomical structure according to a distance between opposed pairs of the plurality of fiducial points.

30. The medium of claim 26, wherein obtaining the image data comprises at least one of obtaining an X-ray image of the at least one internal anatomical structure of the patient, obtaining a venogram image of the at least one internal anatomical structure of the patient, obtaining a fluoroscopy image of the at least one internal anatomical structure of the patient, and obtaining an ultrasound image of the at least one internal anatomical structure of the patient.

31. The medium of claim 26, wherein applying the therapy comprises applying cardiac resynchronization therapy (CRT) to the at least one internal anatomical structure corresponding to a heart of the patient, wherein automatically analyzing the electrical data comprises automatically analyzing the electrical data associated with a respective value of at least one CRT parameter associated with electrical stimulation of the heart of the patient at each of the plurality of iterations to compute an indication of synchrony associated with the heart of the patient, and wherein adjusting the at least one CRT parameter comprises adjusting at least one parameter of the electrical stimulation being delivered to the heart of the patient at each of the plurality of iterations based on the analysis of the electrical data associated with the synchrony of the heart of the patient.

32. The medium of claim 26, wherein the at least one internal anatomical structure corresponds to a heart of the patient; and wherein correlating the electrical data to a corresponding region of interest of the modified model further comprises reconstructing electrical signals on a cardiac envelope of the heart based on the electrical data and geometry data associated with the modified model.

* * * * *